(12) United States Patent
Sindt et al.

(10) Patent No.: US 10,795,182 B2
(45) Date of Patent: Oct. 6, 2020

(54) PROSTHETIC LENSES AND METHODS OF MAKING THE SAME

(71) Applicant: EyePrint Prosthetics LLC, North Liberty, IA (US)

(72) Inventors: Christine W. Sindt, North Liberty, IA (US); Keith D. Parker, Lakewood, CO (US)

(73) Assignee: EyePrint Prosthetics LLC, North Liberty, IA (US)

( * ) Notice: Subject to any disclaimer, the term of this patent is extended or adjusted under 35 U.S.C. 154(b) by 75 days.

(21) Appl. No.: 16/123,965

(22) Filed: Sep. 6, 2018

(65) Prior Publication Data

US 2019/0004333 A1 Jan. 3, 2019

Related U.S. Application Data

(60) Division of application No. 15/367,970, filed on Dec. 2, 2016, now Pat. No. 10,534,197, which is a
(Continued)

(51) Int. Cl.
*A61B 3/00* (2006.01)
*G02C 3/00* (2006.01)
(Continued)

(52) U.S. Cl.
CPC ............ *G02C 7/047* (2013.01); *A61B 3/0025* (2013.01); *A61B 3/107* (2013.01);
(Continued)

(58) Field of Classification Search
CPC ............ A61F 2/145; A61F 2009/00872; A61F 2240/002; A61B 3/107; A61B 3/125;
(Continued)

(56) References Cited

U.S. PATENT DOCUMENTS

| | | |
|---|---|---|
| 5,076,683 A | 12/1991 | Glick |
| 7,682,020 B2 | 3/2010 | Berke |

(Continued)

FOREIGN PATENT DOCUMENTS

| | | |
|---|---|---|
| EP | 2190220 A2 | 5/2010 |
| WO | 2010097089 A1 | 9/2010 |

OTHER PUBLICATIONS

Sindt, Christine W., et al.; U.S. Appl. No. 16/123,959, filed Sep. 6, 2018; Title: Prosthetic Lenses and Methods of Making the Same; 40 pages.

(Continued)

*Primary Examiner* — Mahidere S Sahle
(74) *Attorney, Agent, or Firm* — Conley Rose, P.C.; Grant Rodolph; Robert E. Kent

(57) ABSTRACT

An optical device comprising a lens configured to be disposed in an eye. The lens is configured to contact a sclera of the eye and have a clearance above a cornea of the eye when disposed in the eye. The lens comprises a back surface that comprises at least one non-symmetrical feature that is configured to engage a corresponding feature on the eye. The lens is configured to be rotationally stable in use based on the at least one non-symmetrical feature on the back surface of the lens.

20 Claims, 5 Drawing Sheets

Related U.S. Application Data continuation-in-part of application No. 14/187,036, filed on Feb. 21, 2014, now Pat. No. 9,551,885.

(60) Provisional application No. 61/928,351, filed on Jan. 16, 2014, provisional application No. 61/740,834, filed on Dec. 21, 2012.

(51) Int. Cl.

| | |
|---|---|
| *G02C 7/00* | (2006.01) |
| *G02C 7/02* | (2006.01) |
| *G02C 7/04* | (2006.01) |
| *A61B 3/107* | (2006.01) |
| *B29D 11/00* | (2006.01) |

(52) U.S. Cl.
CPC .. *B29D 11/00105* (2013.01); *B29D 11/00125* (2013.01); *A61F 2240/004* (2013.01); *B29D 11/00086* (2013.01)

(58) Field of Classification Search
CPC .......... G02C 7/047; G02C 7/04; G02C 7/048; G02C 7/02; G02C 7/049; G02C 7/068; G02C 2202/04
USPC .......... 351/159.02, 159.74, 247, 159.01, 212; 623/4.1
See application file for complete search history.

(56) References Cited

U.S. PATENT DOCUMENTS

| | | | |
|---|---|---|---|
| 8,192,020 | B2 | 6/2012 | Goto et al. |
| 8,376,546 | B2 | 2/2013 | Kozu |
| 8,632,188 | B1 | 1/2014 | Gemoules |
| 9,414,906 | B2 | 8/2016 | Blum |
| 9,551,885 | B2 | 1/2017 | Sindt et al. |
| 9,925,038 | B2 | 3/2018 | Yoon |
| 2002/0138070 | A1 | 9/2002 | Peyman |
| 2003/0095232 | A1 | 5/2003 | Mitsui |
| 2004/0075807 | A1 | 4/2004 | Ho et al. |
| 2007/0058829 | A1 | 3/2007 | Unal et al. |
| 2010/0271589 | A1 | 10/2010 | Legerton et al. |
| 2010/0296050 | A1* | 11/2010 | Goto .................... G02C 7/021 351/159.06 |
| 2013/0297015 | A1 | 11/2013 | Johns et al. |
| 2014/0055744 | A1 | 2/2014 | Wildsmith et al. |
| 2017/0082869 | A1 | 3/2017 | Sindt et al. |

OTHER PUBLICATIONS

Marriot, P.J. "Ocular Impressions and Scleral Lens Fitting," Contact Lenses, A Textbook for Practitioners and Students, Dec. 31, 1984, pp. 213-236.

Windecker, R., et al., "Topometry of Technical and Biological Objects by Fringe Projection," Applied Optics, vol. 34, No. 19, Jul. 1, 1995, pp. 3644-3650.

Consejo, Alejandra, et al., "Corneo-Scleral Limbus Demarcation from 3D Height Data", Contact Lens and Anterior Eye, vol. 39, No. 6, Dec. 2016, 8 pages.

Soper, Joseph W.; "Molding and Manufacturing of the Therapeutic Shell"; Corneal and Scleral Contact Lenses Proceedings of the International Congress; The C.V. Mosby Company; Saint Louis; Dec. 1967; 14 pages.

Office Action dated Sep. 11, 2015; U.S. Appl. No. 14/187,036, filed Feb. 21, 2014; 6 pages.

Office Action dated Feb. 10, 2016; U.S. Appl. No. 14/187,036, filed Feb. 21, 2014; 15 pages.

Notice of Allowance dated Aug. 30, 2016; U.S. Appl. No. 14/187,036, filed Feb. 21, 2014; 13 pages.

Office Action dated Apr. 10, 2018; U.S. Appl. No. 15/367,970, filed Dec. 2, 2016; 6 pages.

Office Action dated Jul. 25, 2018; U.S. Appl. No. 15/367,970, filed Dec. 2, 2016; 16 pages.

Foreign Communication From a Counterpart Application, PCT Application No. PCT/US2014/017815, International Search Report dated Sep. 3, 2014, 7 pages.

Foreign Communication From a Counterpart Application, PCT Application No. PCT/US2014/017815, Written Opinion dated Sep. 3, 2014, 10 pages.

Foreign Communication From a Counterpart Application, PCT/US2014/017815, Notification of Transmittal of the International Preliminary Report on Patentability dated Feb. 13, 2015, 26 pages.

Notice of Allowance dated Sep. 19, 2019; U.S. Appl. No. 15/367,970, filed Dec. 2, 2016; 15 pages.

Notice of Allowance dated Dec. 10, 2019; U.S. Appl. No. 16/123,959, filed Dec. 10, 2019; 22 pages.

Sindt, Christine W., et al.; U.S. Appl. No. 16/259,789, filed Jan. 28, 2019; Title: Prosthetic Lenses and Methods of Making the Same; 41 pages.

Sindt, Christine W., et al.; U.S. Appl. No. 16/259,792, filed Jan. 28, 2019; Title: Prosthetic Lenses and Methods of Making the Same; 43 pages.

Final Office Action dated Dec. 10, 2018; U.S. Appl. No. 15/367,970, filed Dec. 2, 2016; 16 pages.

Office Action dated Mar. 1, 2019; U.S. Appl. No. 15/367,970, filed Dec. 2, 2016; 12 pages.

Notice of Allowance dated Jul. 22, 2020; U.S. Appl. No. 16/259,792 filed Jan. 28, 2019; 28 pages.

\* cited by examiner

PROSTHETIC LENSES AND METHODS OF MAKING THE SAME

CROSS-REFERENCE TO RELATED APPLICATIONS

This application is a divisional of U.S. patent application Ser. No. 15/367,970 filed Dec. 2, 2016 entitled "Prosthetic Lenses and Methods of Making the Same", which is a continuation-in-part of U.S. Pat. No. 9,551,885 issued on Jan. 24, 2017, entitled "Prosthetic Lenses and Methods of Making the Same", which claims the benefit of and priority to U.S. Provisional Patent Application No. 61/740,834, filed Dec. 21, 2012, entitled "Prosthetic Lenses," and U.S. Provisional Patent Application No. 61/928,351, filed Jan. 16, 2014, entitled "Prosthetic Lenses and Methods of Making the Same," each of which is incorporated herein by reference in their entirety.

BACKGROUND

In the past (more than 50 years ago), impression molding was done on the eye using a plaster-like substance. A "positive" image was made from the mold using more plaster. A lens was then created by vacuum sealing plastic to the positive mold. A significant amount of time was then spent in post processing of the optics and fit adjustments. The lens did not breathe oxygen and could not be worn very long. In addition, there were problems with this process including shrinking of the mold as it dried, which created a shape very different from the actual eye. Current breathable plastics cannot be vacuum molded.

All contact lens designs currently utilize a series of curves, which approximate the average ocular surface. There are no contact lenses custom fit based on the actual surface of the eye. At this time, all ocular surface evaluation data comes from expensive digital imagery equipment and gives information on a limited surface area, requiring extrapolations of curvatures and prevents customized micro-changes of the posterior contact lens surface.

Scleral contact lenses (large diameter lenses) comprise a subset of gas permeable (GP) contact lenses and completely vault the cornea, landing instead on the scleral part of the eye. Although the original glass scleral contact lenses were first fit in the 1930s, and later molded plastic scleral lenses on the 1950s and 1960s, it was not until the late 1990s that material advancements made their clinical use practical and physiologically tolerable.

Currently available scleral lens are at best semi-custom, and require subjects to sit for extended fitting sessions performed by specialized contact lens eye care providers. Many who suffer from corneal and ocular surface disease are not located near a specialist and incur pricey and repeated travel expenses. These factors are barriers for subjects with corneal disease, and many reach a point where treatment options and visual corrections become very limited.

There is a significant need for a highly customizable oxygen-transmitting device, which follows the contours of an individual eye.

SUMMARY

In an embodiment, a method of obtaining an impression of an eye, the method comprises preparing an impression material, contacting the impression material with an eye of a subject, obtaining an impression of the eye on the impression material, creating an indication of the orientation of the impression with respect to the eye, and removing the impression material from the eye. The method can also include placing the impression material in a bowl of a tray, wherein contacting the impression material with the eye comprises contacting the impression material with the eye when the impression material is disposed within the bowl. The method can also include letting the impression material set for a first time period in the bowl prior to contacting the impression material with the eye. The method can also include aligning the bowl with a predetermined orientation on the eye using an alignment structure. The impression material may comprise a multi-component mixture, and the impression material may comprise a vinyl polysiloxane. The method can also include creating a negative impression of the eye with the impression material.

In an embodiment, a tray for taking an impression of an eye comprises a handle, a bowl, and an alignment structure disposed on at least one of the handle or the bowl. The alignment structure is configured to indicate a relative positioning of the bowl with respect to the eye. The bowl may comprise a side wall defining a conical interior volume. The alignment structure may comprise a flat surface disposed on an exterior surface of the handle, and/or the alignment mechanism comprises a passage at least partially through the bowl. The alignment mechanism may be configured to imprint a mark on an impression material disposed within the bowl. The bowl may have a diameter between about 18 millimeter (mm) and about 28 mm.

In an embodiment, a method of determining a lens design comprises identifying a limbal perimeter within a scanned impression of an eye, determining an optic zone within the limbal perimeter, determining a transition zone adjacent to the optic zone, determining a landing zone adjacent to the transition zone, determining an edge lift zone adjacent to the landing zone, and computing a back lens surface of a lens based on the optic zone, the transition zone, the landing zone, and the edge lift zone. The method can also include scanning a negative impression of an eye in three dimensions, and generating the scanned impression of the eye based on the scanning. The method can also include determining a spindle axis of the lens based on identifying the limbal perimeter. The method can also include determining an optical axis of the lens, wherein the optical axis is not aligned with the spindle axis of the lens. The method can also include computing a distance between the back lens surface of the lens and a surface of the eye as represented by the scanned impression of the eye, and generating a warning when the distance is outside of a predetermined clearance threshold. The method can also include modifying the back lens surface based on one or more bumps identified in the scanned impression of the eye. The method can also include creating a bump zone to account for the one or more bumps, and smoothing the bump zone. The method can also include computing a front lens surface of the lens. The method can also include fabricating the lens based on the back lens surface and the front lens surface.

In an embodiment, a method of manufacturing a lens for an eye comprises receiving one or more data files comprising a back lens surface calculation and a front lens surface calculation, forming a back lens surface from a lens blank based on the back lens surface calculation, forming a front lens surface from the lens blank based on the front lens surface calculation, and forming one or more asymmetric features in the back lens surface based on the back lens surface calculation. The method can also include polishing the lens after milling the back lens surface, milling the front lens surface, and milling the one or more asymmetric features in the back lens surface. The one or more asymmetric features in the back lens surface may comprise an asymmetric landing surface configured to touch a sclera of the eye. The one or more asymmetric features in the back lens surface may comprise one or more bump zone configured to provide clearance for one or more bumps identified on a surface of the eye.

In an embodiment, a lens for an eye comprises a front lens surface, and a back lens surface. The front lens surface and the back lens surface define an interior lens volume, and the lens is not symmetric about a central axis passing through the front lens surface and the back lens surface. The lens may comprise a scleral cover shell. The back lens surface may comprise a central optic zone, a transition zone disposed about the central optic zone, a landing zone disposed about the transition zone, and an edge lift zone disposed about the landing zone. The central optic zone of the back lens surface may comprise a spherical cap shape. The lens can be configured to provide a clearance of between about 100 microns and 500 microns from an outer eye surface in the central optic zone of the back lens surface during use. The transition zone of the back lens surface may have a width of about 2 millimeter. The lens can be configured to provide a clearance of at least about 100 microns from an outer surface of a cornea of the eye in the transition zone of the back lens surface during use. The lens can be configured to contact an outer eye surface in the landing zone of the back lens surface during use. The lens can be configured to provide a clearance of between about 5 microns and 50 microns from an outer eye surface in the edge lift zone of the back lens surface during use. The lens may comprise a gas permeable material. The lens may comprise a multi-focal lens portion. The lens may comprise an independent elevation specific design.

In an embodiment, a lens comprises a contact lens configured to be disposed on an eye, wherein the contact lens comprises: a front lens surface, a back lens surface, and an optical axis. The optical axis is not aligned with a corneal apical axis of the eye. The lens may comprise a scleral cover shell. The lens may comprise a decentered optical design. The lens may comprise a multi-focal lens portion. The lens may comprise an independent elevation specific design.

In an embodiment, an optical lens comprises a lens configured to be disposed in an eye. The lens is configured to contact a sclera of the eye and have a clearance above a cornea of the eye when disposed in the eye. The lens comprises a back surface, and the back surface comprises at least one non-symmetrical feature that is configured to engage a corresponding feature on the eye. The lens is configured to be rotationally stable in use based on the at least one non-symmetrical feature on the back surface of the lens. The corresponding feature on the eye may comprise a protrusion or a deformation, and the at least one non-symmetrical feature on the back surface of the lens comprises a bump zone configured to provide a clearance from the back surface of the lens to the protrusion or the deformation. The at least one non-symmetrical feature on the back surface of the lens may comprise non-symmetric contour configured to follow a contour of the sclera of the eye.

In an embodiment, a method comprises disposing a lens in an eye, contacting a landing zone portion of the lens with a sclera of the eye, and aligning the at least one non-symmetrical feature of the lens with a corresponding surface feature of the eye. The lens comprises a back surface, and the back surface comprises at least one non-symmetrical feature. The lens resists a rotational force based on the alignment of the at least one non-symmetrical feature of the lens with the corresponding surface feature of the eye. The method may also include retaining a weighted portion of the lens in a non-downward position based on the alignment of the at least one non-symmetrical feature of the lens with the corresponding surface feature of the eye. The at least one non-symmetrical feature of the lens may comprise a bump zone on the back surface of the lens, and the corresponding surface feature of the eye may comprise a bump or a deformation of the eye. Aligning the at least one non-symmetrical feature of the lens with a corresponding surface feature of the eye may comprise: aligning the bump zone with the bump or the deformation of the eye; and providing clearance above the bump or deformation of the eye based on the alignment of the bump zone with the bump or the deformation. The lens may also include a marking, and the method may also include aligning the marking with a predetermined position on the eye. Disposing the lens in the eye may comprise disposing the lens in the eye with the marking approximately aligned with the predetermined position on the eye.

In an embodiment, a method of designing a lens comprises scanning a plurality of impressions of a plurality of eyes to create a plurality of eye scan files, storing the plurality of eye scan files in a database, analyzing the plurality of eye scan files to determine one or more average parameters of the plurality of eyes, and designing a lens design using the one or more average parameters of the plurality of eyes. The one or more average parameters comprise at least one non-symmetric feature of the eye. The lens design may comprise a front lens surface design and a back lens surface design. The back lens surface design may comprise the at least one non-symmetric feature of the eye. The at least one non-symmetric feature may comprise an average scleral shape of the plurality of eyes. The method may also include manufacturing a plurality of the lenses using the lens design.

These and other features will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION

Figure 1:
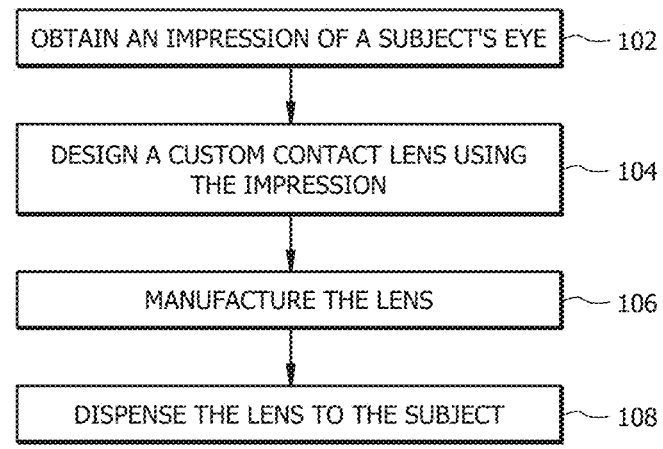
FIG. 1 is a flowchart of a method of providing a lens according to an embodiment.

In the drawings and description that follow, like parts are typically marked throughout the specification and drawings with the same reference numerals, respectively. In addition, similar reference numerals may refer to similar components in different embodiments disclosed herein. The drawing figures are not necessarily to scale. Certain features of the invention may be shown exaggerated in scale or in somewhat schematic form and some details of conventional elements may not be shown in the interest of clarity and conciseness. The present invention is susceptible to embodiments of different forms. Specific embodiments are described in detail and are shown in the drawings, with the understanding that the present disclosure is not intended to limit the invention to the embodiments illustrated and described herein. It is to be fully recognized that the different teachings of the embodiments discussed herein may be employed separately or in any suitable combination to produce desired results.

The purpose of the disclosed embodiments is to provide the best quality of life, through vision, for subjects who are extremely visually impaired and currently without alternative solutions to their corneal disease. The disclosed embodiments are indicated for keratoconus, irregular astigmatism, ocular surface disease (dry eye), trauma, extreme cases of deformed eyes, pellucid marginal degeneration, chemical burns, post-surgical corneas (including corneal transplants and post Laser-Assisted in situ Keratomileusis (LASIK) ectasia), pinguecula, pterygium, stem cell failure, or simply those who desire better vision and comfort. The disclosed embodiments include a prosthetic scleral cover shell, which improves vision by creating a new, smooth, refractive surface for the eye. The lenses produced by the disclosed embodiments, like fingerprints, are unique to each individual.

As shown in FIG. 1, a process 100 for producing a device or lens is illustrated in a flow chart, and each step is described in more detail herein. As used herein, the "device" or "lens" can refer to a prosthetic scleral optical shell with optical qualities, as well as any other type of lens that contacts the eye, such as a retinal contact lens. Initially, an impression of a subject's eye can be obtained at step 102. In an embodiment, the EyePrint Impression Process can be used to obtain the impression of the eye. The EyePrint Impression Process is a relatively simple process that only takes a few minutes to capture the curvatures of the entire eye surface using an impression. This comfortable and gentle process gives more information than high tech computerized topographical scanners and gives doctors the ability to fit complicated patients with precision. The EyePrint Process resulting in the patient specific impression provides details of ocular surface never recognized before in lens design.

Once the impression is obtained, a custom lens can be designed using the impression in step 104. After obtaining the impression, the impression (e.g., the EyePrint Impression) can be shipped to a vendor (e.g., EyePrint Prosthetics LLC) for digitizing and prosthetic scleral cover shell design. Through the latest technology in three-dimensional (3D) scanning and computer controlled machining systems, a match can be achieved to each individual cornea and sclera on a micrometer (i.e., a "micron") scale. Once the lens is designed, it can be manufactured in step 106 and subsequently dispensed to the subject in step 108. Since the lenses disclosed herein can be manufactured using high oxygen permeability material with high quality optics, the wearers can obtain the best in comfort, health, and vision.

The process of taking an ocular impression and then virtual fitting allows a low tech, low cost, simple way for highly complex lenses to be fit by local providers. Recent development of highly oxygen permeable lens materials and a new generation of computer driven lathes make taking a low-tech ocular surface impression to a high tech prosthetic scleral shell possible. Impression materials may include vinyl polysiloxane (VPS), which is also referred to in some contexts as polyvinyl siloxane, or other similar materials known in the art, such as dental impression materials, to create a highly accurate impression of the ocular surface.

In order to generate the impression, an ocular tray may be used along with an impression material. The tray is generally configured to allow the impression material to be placed in contact with the eye to thereby form an impression of the outer surface of the patient's eye. In general, any tray suitable for holding an amount of the impression material in contact with an eye may be used.

Figures 2A, 2B:
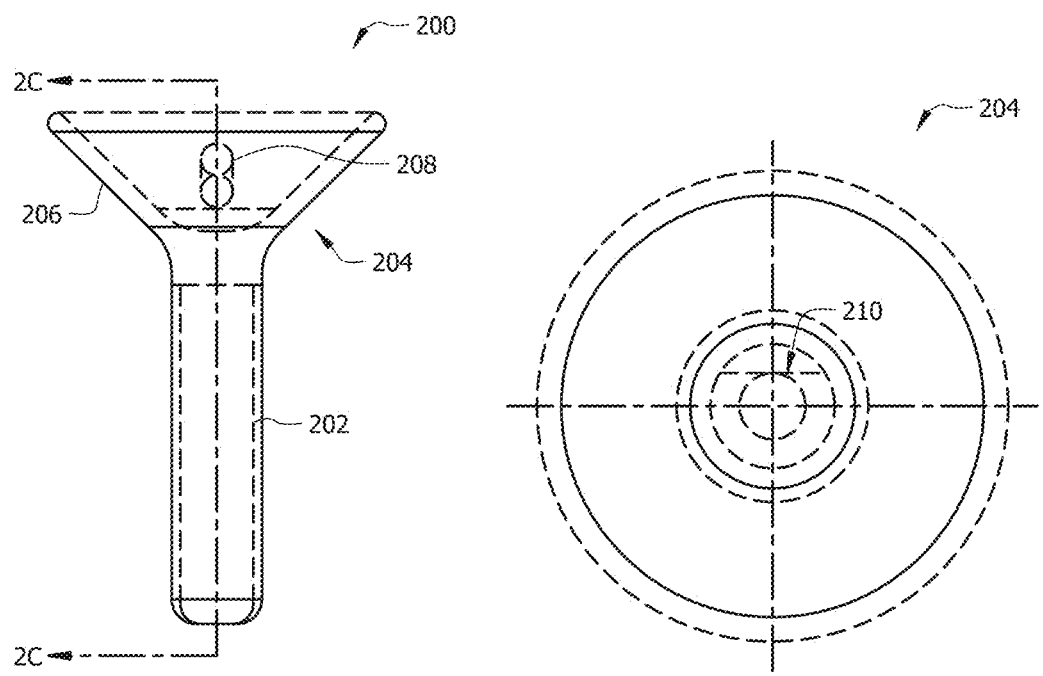
FIGS. 2A-2C are various views of an embodiment of a tray.
Figure 2C:
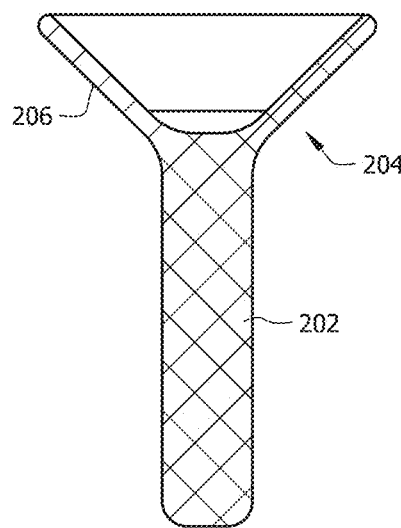
Figure 3:
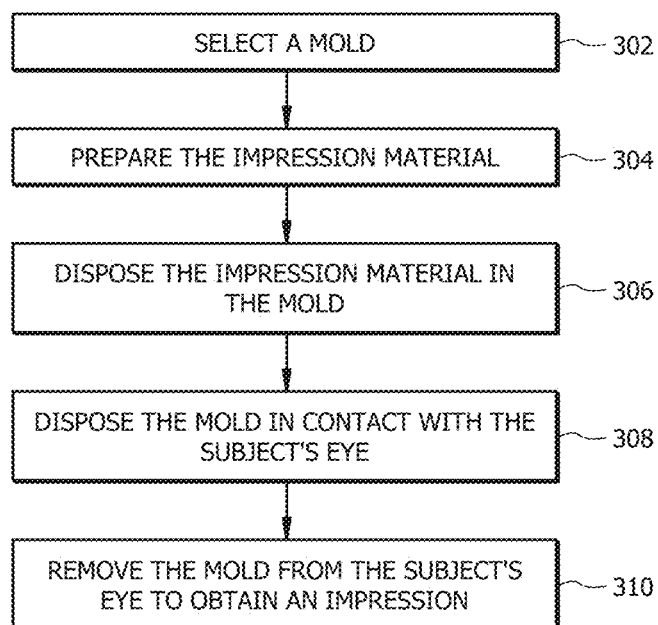
FIG. 3 is a flowchart of a method for obtaining an impression of a subject's eye according to an embodiment.

As described above, the initial step in the process includes obtaining an impression of a subject's eye. In an embodiment, the impression may be obtained in a number of ways, including through the use of a tray and impression compound. An embodiment of a tray 200 is illustrated in FIGS. 2A-2C. The tray 200 generally comprises a handle 202, and a bowl 204. The bowl 204 may comprise a sidewall 206 defining an interior volume. The handle 202 can be used to position and retain the bowl 204 in position during the impression process. The bowl 204 can be used to retain the impression material during the impression process (as described in more detail herein) as well as provide an orientation indication for the impression. In an embodiment, the handle 202 may be oriented along the central axis of the bowl 204 and can be connected at the apex of the bowl 204. The handle 202 may generally comprise a cylindrical shape. An alignment structure or marking may be placed on the handle to aid in orienting the tray 200 during use. For example, a portion of the handle 202 may be flattened to form a flat side 210. In some embodiments, other markings such as raised surfaces, visual indicators, and the like can be used to provide an orientation indicator for the tray 200.

The bowl 204 may generally comprise a relatively straight sidewall 206. As shown in the cross-sectional depiction in FIG. 2A, the side wall 206 may generally be oriented at an angle of between about 60 degrees and about 120 degrees from each other, although other angles may work as well. The sidewalls 206 may generally be symmetric about the central axis of the bowl 204, thereby defining a conical or frusto-conical volume within the bowl. The outer ends of the sidewall 206 may be rounded or otherwise smoothed to prevent injuring the eye when the end is placed in contact with the eye. In general, the outer end of the bowl 204 may be sized to allow the bowl 204 to be paced in contact with the eye of a subject and cover at least the cornea and a short distance out onto the sclera. For most subjects, the outer end of the bowl 204 may generally have a diameter ranging from about 15 mm to about 30 mm, or about 18 mm to about 28 mm (e.g., 18 mm, 22 mm, 26 mm, etc.), although other sizes may work as well. In some embodiments, a plurality of trays having bowls of different diameters may be available to allow a suitable size to be selected for a given subject.

As seen from the top view illustrated in FIG. 2B, the outer end of the bowl 204 may define a substantially circular contact surface with the eye. While illustrated as being circular, other round shapes (e.g., elliptical, oblong, etc.) may also be used. In embodiments, the bowl is configured to cover the eye including the optic zone within the limbal perimeter as well as at least a short distance beyond the limbal perimeter.

In some embodiments, the bowl 204 may comprise an alignment structure or marking. The alignment structure in the bowl 204 may serve to aid in aligning the bowl during the impression process and/or forming a marking in the impression itself for later use during the lens manufacturing process. The alignment structure on the bowl 204 may be used in place of or in addition to the alignment structure on the handle 202. In an embodiment, the alignment structure may comprise a hole or passage 208 through the sidewall 206, and the impression material may protrude into and/or out of the passage 208. When used along with an alignment structure or marking on the handle, the passage 208 may be aligned with the alignment structure on the handle. For example, the passage 208 may be aligned with the flat surface 210 on the handle to allow for ease of alignment when using the tray 200.

The tray 200, or one or more portions thereof, may be made from any suitable material. While opaque materials may be suitable, the use of a transparent or semi-transparent material may help to align the tray on the eye of the subject during use. For example, the tray 200 may be formed from glass, plastic (e.g., a medium or high impact polymer such as an acrylic), a composite, or the like.

The tray 200 is configured to retain the impression material. The impression material can be configured to be deformable when contacted with the eye, and the impression material may or may not increase in viscosity after being contacted with the eye. The impression material is generally selected to avoid irritation to the eye when placed in contact with the eye. In some embodiments, the impression material may chemically react to harden or increase in viscosity, thereby "setting" after being contacted with the eye. For example, the impression material may be contacted with the eye and left in contact with the eye while the material at least partially sets and/or be removed to allow the impression material to set or continue to set.

In some embodiments, the impression material may comprise a low viscosity, addition polymerizing material such as a vinyl polysiloxane impression material, which has been used in dental work. One suitable impression material is sold by the trade name Tresident 2000 DH available from Schutz Dental GmbH of Germany. The impression material may have hydrophilic properties to provide good contact with the eye and the features on the surface of the eye. When the impression material is configured to set, the impression material can be provided as one or more fluids within a cartridge that can be mixed and injected by a universal dispenser. The use of a multi-component impression material may allow the impression material to be prepared at or near the time the impression is to be made.

In use, the impression may be obtained using the tray 200. Initially, the subject or patient is prepared for the impression process. For example, the subject can be placed in a supine position and asked to fixate on a point (e.g., on a point on a ceiling). If the subject has a high refractive error, the subject may use a spectacle trial lens in front of the fixating eye. The subject may generally be made aware of the procedure to prepare them for the process.

With reference to FIGS. 2A-2C and FIG. 3, a method 300 of obtaining an impression may begin by selecting a tray 200 at step 302. In general, the tray 200 may be selected to have the largest diameter that can easily be inserted between the lids of the particular subject. As noted above, the tray 200 may comprise bowls 204 having a range of sizes, and the appropriately sized bowl 204 may be selected. The flat edge 210 of the handle 202 can correspond to the passage 208 (e.g., a fenestration) of the bowl 204. The passage 208 of the bowl 204 can be placed at the 12 o'clock position on the eye. The orientation of the bowl is used to generate the lens as well as an indication of the orientation of the lens.

The impression material can then be prepared at step 304 and placed in the bowl at step 306. When the impression material is a single component, it may be placed in the interior volume of the bowl 204. When a multi-component impression material is used, it may be mixed and placed in the bowl 204. For example, when the impression material is supplied as a liquid, multi-component mixture in separate containers or cartridges, the cartridges and impression material may be placed in a universal dispenser. Any lids or seals may be removed and a small amount of the impression material may be extruded from the cartridges to determine that the material flows uniformly from both openings. A mixing tip may be used to combine the multi-component impression material as it is extruded from the cartridges. Once the impression material is ready, it may be disposed in the bowl 204. The bowl 204 may be filled so that the impression material can contact the eye over the entire surface defined by the outer end of the bowl 204.

When an impression material is used that sets, it may be allowed to set for a short time (e.g., 30 seconds to 2 minutes, or about 60 seconds) before it is ready for use. When the impression material is ready, the tray 200 having the bowl 204 with the impression material within it can be placed into contact with the subject's eye. In some embodiments, a topical anesthetic may impair the quality of the impression, and as a result, the impression material may be placed directly in contact with the eye without any anesthetic being applied.

The bowl 204 may be placed in contact with the eye at step 308. In an embodiment, the bowl 204 may be placed between the eyelids with the alignment passage 208 aligned at the 12 o'clock position. The tray 200 can be applied with enough pressure so that the impression material completely rest over the area under the bowl 204. The pressure should be less than an amount that would distort the corneal curvature. Some impression material may be displaced outside of the bowl 204. The subject can fixate on the point to maintain the eye relatively stationary during the impression process. The tray may be maintained in contact with the eye for a time period sufficient to impart the impression of the eye on the impression material so that the impression is maintained when the tray is removed. In an embodiment, the bowl may be maintained in contact with the eye between about 30 seconds and about 3 minutes, or about two minutes.

When the impression can be retained by the impression material, the tray 200 can be removed from the subject's eye in step 310. In order to break a seal that may have formed between the impression material and the eye, the bowl 204 may be gently lifted by a single edge while the eye can be indented to break any suction. The bowl and impression material can be configured to have a greater bonding strength than the impression material and the eye. As a result, the impression material should generally adhere to the bowl 204 rather than the eye when the tray 200 is removed, and should not distort when removed from the eye or during the curing process. The eye can then be inspected to ensure that the impression material has been removed and that no injury to the eye has been caused by the impression process. The process may be repeated for the other eye of the subject if needed. In general, it is expected that the impression material can be reused for each eye and/or multiple subjects.

The impression may be retained within the bowl 204 to allow the impression to cure or harden further. In general, the impression may be maintained within the bowl 204 while the impression is sent for scanning, as described in more detail below. A cover or case may be used to protect the impression in the bowl 204 from damage to the impression surface during shipment. In the event that the impression is separated from the bowl 204, the passage 208 (e.g., a fenestration) in the bowl 204 may create a marking on the impression to indicate how the impression is oriented within the eye. For example, the impression material may displace into the passage 208 during the impression process. If the impression is removed from the bowl 204, a post or tag may indicate the position of the passage 208 relative to the impression. Other features on the interior of the bowl 204 may also be used to provide an indication of the orientation of the bowl relative to the eye.

The result of the impression process is a negative impression of the outer surface of the subject's eye formed in the impression material. The use of the impression material may allow for small details of the eye to be captured. Further, the impression material may be selected so that the impression does not shrink or change dimensions upon setting, thereby providing a high definition representation of the outer surface of the eye. Various features of the eye can then be identified in the negative impression. For example, the negative impression may allow the optic zone, transition zone, landing zone, and lifting zone to be identified by representing the limbal perimeter and/or one or more surface features (e.g., bumps, indentions, protrusions, irregular shapes, etc.) of the eye, as described in more detail below. The resulting negative impression can then be sent for further processing for the scleral cover shell to be produced.

Figure 4:
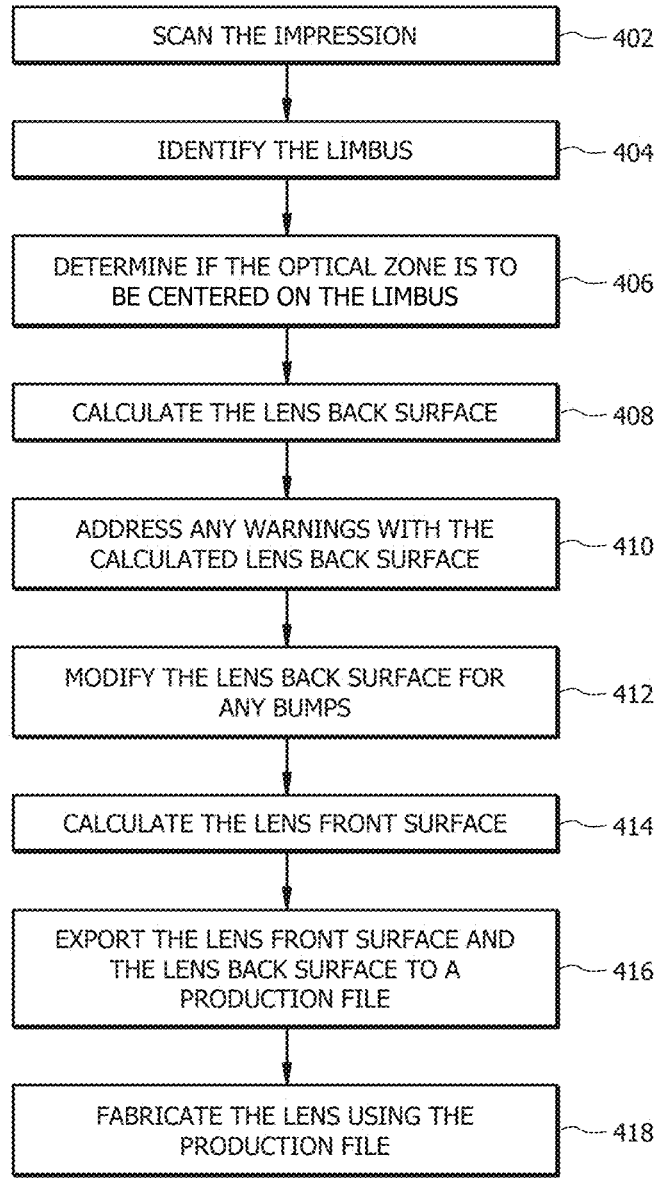
FIG. 4 is a flowchart of a method for designing a lens according to an embodiment.

The impression can then be used to design and fabricate a lens for the subject based on the mold. As illustrated in FIG. 4, a method 400 of designing and fabricating the lens may begin by scanning the impression at step 402. In order to create the lens (e.g., a scleral cover shell), the impression (e.g., a negative mold) of the eye can be scanned into 3D space and a file can be created containing a set of 3D points (e.g., X, Y, Z coordinates). The scanning can comprise a resolution sufficient to identify the surface features of the eye. In an embodiment, the scan of the eye may have a resolution ranging from about 1 micron to about 500 microns, about 4 microns to about 100 microns, or about 7 microns.

In some embodiments, the points may be stored in a binary format in a stereolithiography (STL) file. The file may be accessible by a suitable application such as the applicant's EyePrint Designer Software (EPDS). The application can convert the negative image of the surface of the eye to a positive image. The application may execute on a processor and can use an input STL file generated by the 3D scanner. The file can be displayed in the 3D space, and various editing tools may be available to prepare the 3D object for the design of the lens.

The application can include an application or a wizard that guides the user from the selection of the eye mold to the generation of the production files, which can be used with a lathe, mill, or 3D printer to create the lens. For example, the production files can be used with a Computer Numerically Controlled (CNC) 2-axis lathe with Oscillating Tool Technology (OTT) and/or a DAC ALM OTT lathe (e.g., available from DAC Int. Inc. of Carpinteria, Calif.) to prepare the lens. During the successive steps of the lens design, the mold and both lens surfaces can be displayed in the 3D space using a 3D viewer that lets the user zoom in and out, rotate, orient the view, and adjust the transparency of the surfaces that are displayed.

Figure 5A:
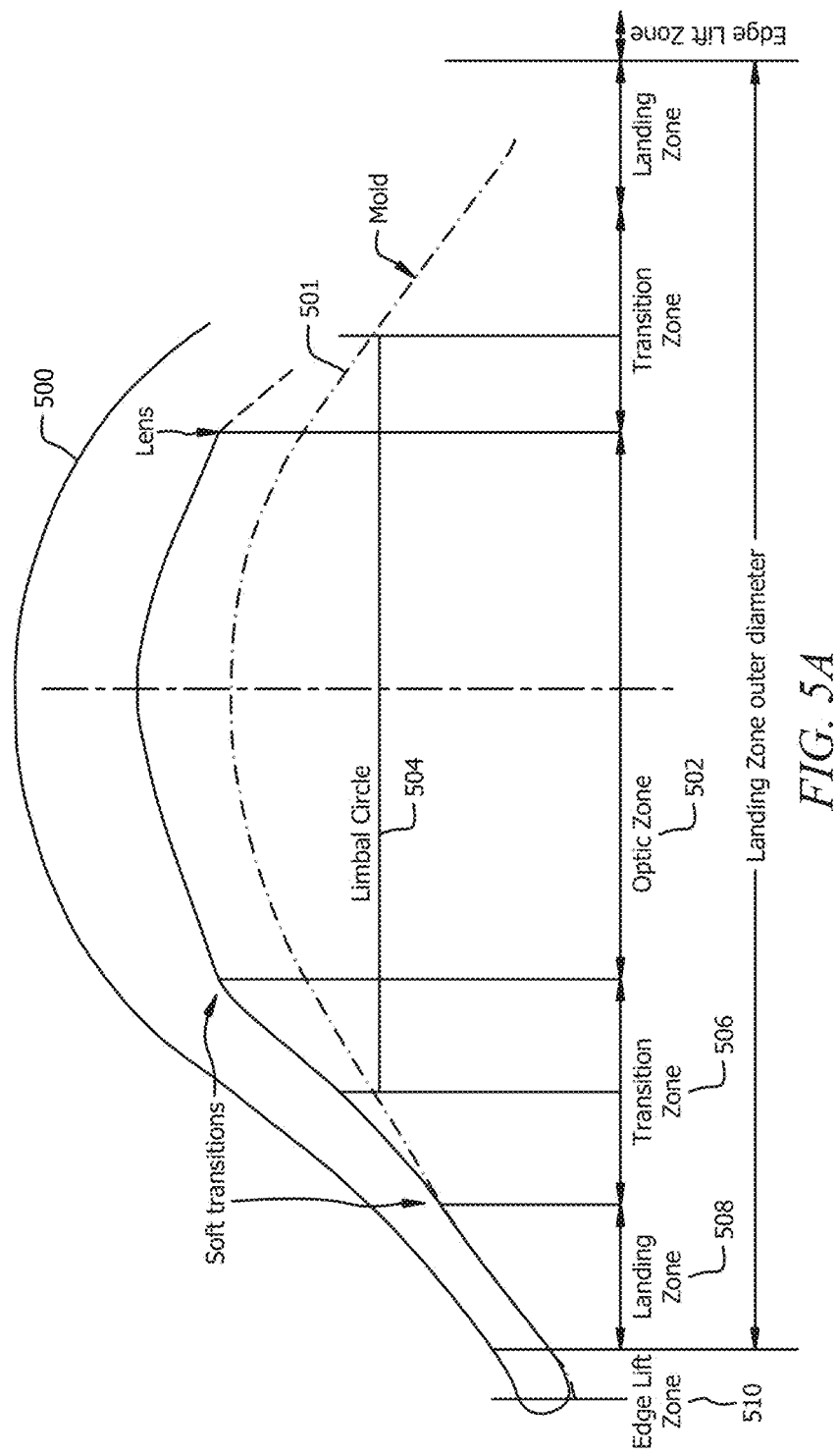
FIGS. 5A and 5B are schematic diagrams of a tray and a lens according to an embodiment.
Figure 5B:
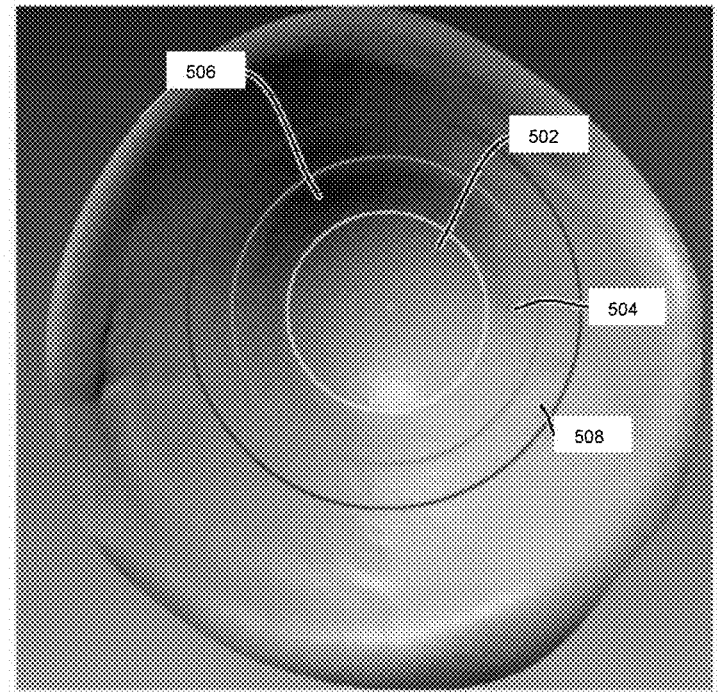

The application generally allows for an identification of the zones of the eye and generates a production file that defines the inner and outer surfaces of the lens. The production file can then be used to prepare the lens for the user using one or more production techniques. In order to illustrate the lens design process, reference is made to FIGS. 5A and 5B, which illustrates the various zones and features of the inverted mold 501 (i.e., the positive image of the negative impression) of the corresponding eye and the lens 500. Specifically, FIG. 5A illustrates a partial cross-sectional, side view of a lens on a mold (which may also represent an eye), and FIG. 5B illustrates a bottom view of the lens on the mold. The mold 501 can be used to identify several features of the eye including, but not limited to, the limbal perimeter 504 and/or one or more surface features. Corresponding zones can be defined including the optic zone 502, a transition zone 506, a landing zone 508, and an edge lift zone 510. The limbus is considered the border between the cornea and the sclera and can be described by reference to the limbal perimeter 504.

The optic zone 502 represents the area where light enters the eye through the cornea and is generally defined as being within the limbal perimeter 504. In an embodiment, the optic zone 502 can be defined as being entirely within the limbus, for example, about 1 mm inside the limbus. Since the border between the cornea and sclera is generally not sharp, the transition zone 506 can be defined to capture the limbal perimeter 504. In an embodiment, the transition zone 506 may have a width of about 2 mm and encompass about 1 mm inside the limbus to about 1 mm outside the limbus. In general, the lens 500 will have a clearance from contacting the cornea within the optic zone 502 and the transition zone 506. The "clearance" refers to the distance between the surface of the eye and the inner surface of the lens 500. In an embodiment, the lens 500 may have a clearance between about 100 microns and about 400 microns from the eye (e.g., the cornea) in the optic zone 502. In an embodiment, the lens 500 may have a clearance between about 100 microns and about 400 microns from the eye at the border with the optic zone 502 and may be touching the eye at the border with the landing zone 508.

The landing zone 508 is a continuation of the transition zone 506 and can be defined as a region outside of the transition zone 506. The landing zone 508 may include a region in which the lens enters into contact with the sclera. In an embodiment, the landing zone 508 may have an outer diameter ranging from about 15 mm to about 20 mm, or about 18 mm. The edge lift zone 510 is a continuation of the landing zone 508 and may be tangent to the surface of the eye at the intersection with the landing zone 508. The edge lift zone 510 may have a clearance from the sclera to allow the lens to be lifted off the eye. In an embodiment, the edge lift zone 510 may have a width of between about 0.25 mm and about 1.00 mm, or about 0.5 mm. The edge lift zone 510 may have a clearance from the sclera of between about 10 microns and about 50 microns, or about 25 microns at the outer edge of the edge lift zone 510 and may be touching the eye at the border with the landing zone 508.

Referring to FIG. 4 and FIGS. 5A and 5B, the limbus can be identified and localized using the application in the second step 404 of the lens design process. Using the application, the user can define at least 3 points lying on the limbus. The application can then automatically define a limbal perimeter 504 based on fitting a perimeter to the points. The limbus and the limbal perimeter 504 may take the form of any shape, typically one bound by a generally rounded perimeter (e.g., an oval, an ellipse, a torus, a circle, an egg shape, etc.). The shape of the limbus and limbal perimeter 504 may be symmetrical about any one or more axis and/or may be non-symmetrical about any one or more axis. As such, the limbal perimeter 504 is not limited herein to a circle or circular shape. In an embodiment, the application can execute a circular regression or other perimeter or shape fitting algorithm to calculate the perimeter that best fits to the identified points. More points can be included on the limbus by the user to fine-tune the position of the perimeter. When more than three points are present, the distance from the calculated perimeter and the points can be minimized to best fit the perimeter to the points. For example, the sum of the square Euclidian distances between each point and the perimeter can be minimized to fit the perimeter to the points. The resulting position of the limbus is used to determine the spindle axis, which can be identified as an axis perpendicular to the plane of the perimeter and passing through a center point of the perimeter. In some embodiments, the spindle axis can be offset from the center point of the perimeter. In an embodiment, the calculation of the limbal perimeter 504 may also allow the 3-D representation of the mold to be re-oriented if the mold is not oriented correctly during the scanning process.

In a third step 406, the user can specify if the optic zone 502 should be centered on the limbus or not. In general, several axes can be defined for the eye. The optical axis refers to an axis passing through the center of the optic zone of the lens. The visual axis refers to a line of site where a beam of light would enter the eye and extend to the phobia on the retina. Finally, the corneal apical axis refers to an axis passing through the geometric center of the dome forming the cornea. In general, the optical axis of the device and the visual axis should align to provide the highest quality sight for a subject. When the optic zone 502 is centered, the spindle axis as defined by the optic zone 502 may align with the optical axis and/or the visual axis. When the optical axis is decentered, the axis may be defined independently of the spindle axis. In the event of decentered optic zone 502, the center of the optic zone 502 can be manually positioned using the 3D viewer, or by manually specifying the distance to the limbus center and the angle. For example, the center of the optic zone 502 can be aligned with the optical axis, the visual axis, and/or the corneal apical axis. The optic zone 502 diameter can be calculated based on the distance between the optic zone 502 center and the limbus.

Once the optic zone 502 is defined, the application can compute (e.g., automatically compute) the lens back surface in a fourth step 408, where the lens back surface may be defined by four zones. First, the optic zone 502 can be assumed to be a 3D spherical cap. The optic zone 502 can be represented as a perimeter in a bottom view that is centered on the optic zone center (e.g., as defined in the second step above). The optic zone 502 perimeter may have a size that is sufficient so that the optic zone 502 perimeter is about 1 mm inside the limbal perimeter 504. In a side view, the optic zone 502 can have a circular arc shape, whose radius is approximately equal to the radius of the cornea. In an embodiment, the optic zone 502 edge clearance and/or the center clearance can be specified, and the application can calculate a spherical shape conforming to the clearances.

In the event of a centered optic zone 502, the inner surface of the lens may have a clearance of between about 100 microns and about 500 microns, or between about 350 microns and about 450 microns (e.g., about 400 microns) above the optic zone center, and the border may also have a clearance of between about 350 microns and about 450 microns (e.g., about 400 microns) above the cornea. In the event of a decentered optic zone 502, the inner surface of the lens may default to about 400 microns above the optic zone border. The radius of the inner surface of the lens can then be matched to the radius of the cornea, which can determine the clearance of the inner surface of the lens above the center of the optic zone 502. Various checks can be performed to ensure that the clearance of the inner surface of the lens above the center of the optic zone 502 for a decentered optic zone 502 is greater than a minimum clearance threshold. In an embodiment, the minimum clearance threshold may be between about 50 microns and about 150 microns, for example about 100 microns. If the clearance between the inner surface of the lens and the outer surface of the eye is below the minimum clearance threshold, the clearances, shape, and location of the optic zone 502 can be altered to allow for the minimum clearance threshold.

Second, the transition zone 506, between the optic zone 502 and the landing zone 508, is a continuation of the optic zone 502. In a bottom view, the transition zone 506 is represented as a ring shape that is centered on the spindle axis. The transition zone 506 starts from the optic zone 502 edge and has an approximate width of about 2 mm (e.g., starting 1 mm inside the limbus and extending to about 1 mm outside the limbus). In a side view, the transition zone 506 portion of the lens has a profile approximated by a polynomial shape that is connected to the optic zone on the inner side and lands on the sclera on the outer side. At the junction with the optic zone 502, the transition zone 506 has a clearance of about 400 microns, and the transition zone 506 contacts the sclera on the outer edge. Within the transition zone 506, the inner surface of the lens may have a clearance of between about 50 microns and about 150 microns (e.g., about 100 microns) above the limbal perimeter stem cells. The clearance above the limbal perimeter may help avoid any irritation of the limbal stem cells, which can cause discomfort, inflammation, and/or disease for the subject. The shape of the transition of the inner surface of the lens from the optic zone 502 to the transition zone 506 may be softened or rounded to avoid any abrupt changes in the direction of the inner surface of the lens (e.g., first derivative changes). In an embodiment, the transition may be softened by using surface computations, setting maximum direction change angles, and/or using a minimum junction blend radius. For example, the shape of the transition zone 506 can be computed using Bezier curves to enforce first derivative continuity at each junction. The application can calculate the clearance between the inner surface of the lens and the eye at each point in the transition zone 506. If the inner surface of the lens contacts the cornea at any point before reaching the landing zone 510, a warning may be generated and the transition zone diameter and/or clearances can be modified to prevent the lens from contacting the cornea. In some embodiments, when the clearance between the inner surface of the lens and the eye falls below a minimum clearance threshold, the shape of the inner surface of the lens in the transition zone 506 may be divided into two or more consecutive Bezier curves that satisfy the continuity at the optic zone 502 and landing zone 508 interfaces while allowing for the clearances defined by the minimum clearance threshold(s).

Third, the landing zone 508 is a continuation of the transition zone 506 and can be defined as a surface that contacts the eye and aligns with the sclera supporting the weight of the lens on the eye. In a bottom view, the landing zone 508 is represented as a ring shape that starts at the outer edge of the transition zone 506 and extends to an outer diameter of between about 15 mm and about 25 mm, between about 16 mm and about 20 mm, or about 18 mm. In a side view, the landing zone 508 has an approximately arcuate shape that lies in contact with the sclera.

Fourth, the lens back surface is completed by an edge lift zone 510 to allow for easy removal and improved comfort. The edge lift zone 510 is a continuation of the landing zone 508 and comprises a clearance from the sclera to allow the lens to be lifted off the sclera. The lens back surface in the edge lift zone 510 can be defined by Bezier curves to ensure a smooth transition at the landing zone 508 interface and a reduced or minimum curvature on the lens outer diameter. In a bottom view, the edge lift zone 510 is represented as a ring shape that starts at the outer edge of the landing zone 508 and has a width between about 0.1 mm and about 2 mm, for example, about 0.5 mm. In a side view, the edge lift zone 510 has a circular arc shape. The lens may be tangent to, and in contact with, the sclera at the inner edge of the edge lift zone 510, and the lens may transition to a clearance at the outer edge of the lens in the edge lift zone 510. In an embodiment, the lens may have a clearance between about 5 microns and about 50 microns, or between about 20 microns and about 100 microns at the outer edge of the lens in the edge lift zone 510.

Each of the optic zone 502, the transition zone 506, the landing zone 508, and the edge lift zone 510 may take the form of any shape, typically one bound by a generally rounded perimeter (e.g., an oval, an ellipse, a torus, a circle, an egg shape, etc.). The shape may be symmetrical about any one or more axis and/or may be non-symmetrical about any one or more axis. Furthermore, any one or more of the limbal perimeter 504, the optic zone 502, the transition zone 506, the landing zone 508, and the edge lift zone 510 may have a same shape as another zone or may have a different shape as another zone. In one embodiment, each of the limbal perimeter 504, the optic zone 502, the transition zone 506, the landing zone 508, and the edge lift zone 510 may have substantially a same shape. In another embodiment, each of the limbal perimeter 504, the optic zone 502, the transition zone 506, the landing zone 508, and the edge lift zone 510 may have different shapes such that no two zones have substantially the same shape. In yet another embodiment, any first plurality of the limbal perimeter 504, the optic zone 502, the transition zone 506, the landing zone 508, and the edge lift zone 510 may have a substantially same first shape while any second plurality of the limbal perimeter 504, the optic zone 502, the transition zone 506, the landing zone 508, and the edge lift zone 510 may have a substantially same second shape.

The lens back surface can be automatically calculated when the clearances and widths are set in the application. Upon calculating the lens back or inner surface, a representation of the inner surface of the lens can be displayed in a 3D viewer. The user can manually tune each zone clearance and diameter, and see the changes in real time in the 3D viewer.

The application may raise warnings based on the computed lens back surface and the surface of the mold 501 in an optional fifth step 410. In an embodiment, the application may determine a clearance between the back of the computed lens and the surface of the mold 501. Warnings can be generated based on the distance between the inner surface of the lens and the mold either falling under a given minimum clearance threshold or resulting in contact. In an embodiment, clearance ranges may be established for the optic zone 502, the transition zone 506, and/or the edge lift zone 510. When the computed clearances between the inner surface of the lens 500 and the mold fall outside of these ranges, the application may generate a warning message. Similarly, when the back surface of the lens touches the mold at one or more designated points, the application may generate a warning message. When a warning message is generated, the user may redefine the lens shape (e.g., clearances, diameters, etc.) to address the warning so that all of the distances fall within the established ranges or thresholds.

In a sixth step 412, the user has the possibility to define bumps, i.e. small peaks on the eye needing extra clearance. The process is semi-automated, and the user can adjust the size and the clearance of each bump. For example, when the application identifies one or more points lacking the necessary clearance, the user may modify the design of the lens to reduce or eliminate the lack of clearance. For bumps located in the optic zone 502 and/or the transition zone 506, the application may identify one or more points having clearances below the applicable minimum clearance thresholds, which may indicate the presence of a bump. In order to address the bumps in these locations, the clearances at the respective points may be adjusted. For example, the inner surface of the lens may be designed with a corresponding indentation to provide the appropriate clearance at the location of the bump(s). In addition to altering the clearances, the default clearances in the corresponding zone and/or the outer diameters of the zones can be altered to adjust for the presence of one or more bumps.

Bumps occurring in the landing zone 508 are located, by definition, on the sclera. The default calculation for the landing zone 508 can include a rotationally symmetrical shape. When the calculations indicate that a bump exists that has less than a minimum threshold clearance, the lens design can be altered to account for the bump. In an embodiment, a bump can be taken into consideration by creating an inner lens surface that provides room for the bump. A bump zone can be defined by identifying the center of the bump. For example, the highest point of the bump may be identified by a user or the application can automatically determine the point having the minimum clearance. The bump zone can be represented as a circular zone (e.g., defining a dome) having a radius and a central height that is sufficient to provide the minimum clearance above the bump, which may be in contact with the peak of the bump. The combination of the radius and height of the bump zone may be used to create a clearance around the bump on the sclera in the landing zone 508. When two or more bumps are close together, the bump zone may cover a plurality of bumps. For example, the radius and height of the bump zone may provide a clearance for two or more of the bumps that are sufficient close together. The bump zone may then be placed into the lens inner surface calculation.

After computing the back surface and making any modifications for any bumps, the application may compute (e.g., automatically compute) the lens front surface in a seventh step 414. The user can define the lens material refractive index, the spherical amount of the target prescription, cylinder powers (toric design), and the lens thickness. The application can apply optical formulas to calculate the front surface curvature in the optic zone 502, which may generally comprise a spherical cap with any corrections for the prescription. In a bottom view, the front surface in the optic zone 502 is generally circular and has a center matching the center of the back surface of the optic zone 502 (e.g., a centered optic zone 502 or a decentered optic zone 502). In a side view, the front surface of the optic zone 502 can have a generally circular arc shape having a radius of curvature sufficient to allow the lens to have a thickness between about 0.25 mm and about 0.75 mm, or between about 0.4 mm and about 0.5 mm (e.g., about 0.45 mm) in the center of the optic zone 502. The lens may have a decreased thickness on the edge of the optic zone 502. In an embodiment, the lens may have a thickness between about 0.15 mm and about 0.5 mm, or between about 0.25 and about 0.3 mm (e.g., about 0.28 mm) on the edge of the optic zone 502 (e.g., at or near the border with the transition zone 506). Once the optic zone 502 thickness is determined, the front surface shape can be altered, while maintaining the thickness at the center of the optic zone 502, to integrate the prescription cylinder amount. Since the lens cylinder power is generally less than its sphere power, the boundary thicknesses should still satisfy the predetermined thickness thresholds after this alteration.

In an embodiment, the lens front surface calculation can calculate a reduced thickness for the lens in the optic zone 502. The application may initially calculate a front surface curvature in the optic zone 502. The resulting thickness of the lens in the optic zone 502 can then be calculated and checked against a predetermined thickness threshold. If the front surface curvature is such that the thickness of the lens at the boundary of the optic zone 502 is below the predetermined thickness thresholds, the application can increases the thickness of the lens in the center of the optic zone 502. The increased thickness can alter the computed front surface curvature, and therefore the resulting boundary thickness. This process may iterate until a center thickness is achieved, wherein the center thickness also satisfies the predetermined thickness threshold, for example, at the optic zone 502 boundary with the transition zone 506. In some embodiments, this process can be used to find the thinnest lens thickness in the optic zone 502 that satisfies the predetermined thickness thresholds.

The front surface calculation for the lens in the transition zone 506 can be calculated in a number of ways. The front surface of the lens in the transition zone 506 represents a continuation of the optic zone 502, and matches the front surface of the optic zone 502 at the boundary between the two zones. In a bottom view, the transition zone 506 is generally circular and the outer border of the transition zone 506 can be centered on the spindle axis. The inner border of the transition zone 506 on the front surface is calculated to match the outer border of the front optic zone 502. In a side view, the profile of the front surface in the transition zone 506 is generally non-spherical in shape. The thickness of the lens at the border between the optic zone 502 and the transition zone 506 is described above. The lens may transition to a thickness between about 0.1 mm and about 0.3 mm, or between about 0.15 mm and about 0.25 mm (e.g., about 0.2 mm) at the outer border of the transition zone 506.

The front surface calculation for the lens in the landing zone 508 can be calculated in a number of ways. The front surface of the lens in the landing zone 508 represents a continuation of the transition zone 506, and matching the front surface of the transition zone 506 at the boundary between the two zones. The front surface of the lens in the landing zone 508 extends to cover both the landing zone 508 and the edge lift zone 510. Thus, the outer edge of the landing zone 508 on the front of the lens extends to the outer edge of the lens. In a bottom view, the front surface of the landing zone 508 has a circular, ring shape that is centered on the spindle axis. The inner border of the ring forming the landing zone 508 may match the back lens surface landing zone 508 inner border, and the outer border of the ring forming the landing zone 508 may match the back-surface edge lift zone 510 outer border. In a side view, the front surface of the lens in the landing zone 508 may have a non-spherical shape. The lens may have a thickness between about 0.1 mm and about 0.3 mm, or between about 0.15 mm and about 0.25 mm (e.g., about 0.18 mm) in the landing zone 508. The outer edge of the lens may have a rounded shape to avoid any sharp edges contacting the eye.

The application can calculate the front surface and then display the lens back and front surfaces in the 3D viewer to let the user see the lens. If any corrections or changes are needed, the user can modify the radius and/or thickness of any zone. In an embodiment, a user can use the 3D presentation to verify the calculations of the lens prior to finalizing the lens design. In general, the resulting lens design resulting from the front and back surface calculations can be non-rotationally symmetrical design. Further, the customization for each subject may result in a lens that may fit in a specific orientation during use, which may allow for additional prescriptions and designs that have not previously been achievable in a lens design.

In an eighth step 416, the back and front surfaces are then exported as a set of two data point production files, one for each surface, thereby defining the lens. Information identifying the subject may also be included as a separate file or within one or more of the data point production files. In some embodiments, the files may be combined into a single production file. The production files may be in a format suitable for use in fabricating the lens, for example, suitable for use with a lathe, a milling machine, and/or 3D printing machine.

The surface files can be determined by converting the computed surfaces to a set of rings centered on the spindle axis. The rings can be used to build 3D meshes that can be displayed in the 3D viewer as well as to generate the production files. Viewing of the 3D surfaces allows the user to visually check that the calculated production surfaces match the calculated surfaces from the application.

In a ninth step 418, the lens may be fabricated using any suitable fabrication technique or method. In an embodiment, the lens may be fabricated using a lathe or mill to create the lens from a lens blank. In this process, a lens blank having a suitable starting shape may be placed in a lathe or mill. For example, a lens blank may comprise a cylindrical section of lens material. In an embodiment, the lens material may comprise a flexible or rigid gas permeable material (e.g., an oxygen permeable material) suitable for use with an eye. Suitable materials can include, but are not limited to, silicone hydrogel, silicone, a silicone derivative (e.g., a silicone acrylate), polymethyl methacrylate (PMMA), fluorosilicone acrylates, and/or any combination thereof.

The lathe or mill may use the production file to guide the lathe or mill and remove a portion of the lens blank. In order to produce a custom lens, the lathe or mill may be capable of creating a non-rotationally symmetric surface on the front, and/or back of the lens. For example, a lathe may comprise an oscillating tool technology to allow non-symmetric shapes to be created in the lens. The removal of material from the lens blank may result in the formation of a lens for the subject that is specific to the impression formed for the eye. One or more post formation processes may be used to further prepare the lens for the subject. For example, the lens may be further polished, coated, treated, or the like to prepare it for use by a subject.

The resulting lens produced by the impression, design, and lathing process may provide for a number of unique properties. In an embodiment, the lens may be non-symmetric about a rotational axis. This may allow for different curvatures in the landing zone to match the contours of the subject's eye. In general, the sclera is not rotationally symmetric, and the use of the impression may allow the specifics of a subject's eye to be taken into consideration in the design of the lens.

Further, the lens may comprise non-symmetric features. For example, the optical axis can be decentered and the lens may have features specific for one or more bumps or other irregularities in the eye. This may be described in some contexts as utilizing an X, Y, Z coordinate system, where each point on the inner and outer surface of the lens can be independently varied. As used herein, the Z axis is parallel to the spindle axis, and the X and Y coordinate axes are aligned perpendicular to the Z axis to define a Cartesian coordinate system perpendicular to the Z axis. In traditional lens designs, the lenses were rotationally symmetric about the spindle axis so that at any given X and Y coordinate, the Z coordinate was symmetric about the spindle axis. Thus, the lens described herein may have a Z coordinate that varies about the spindle axis (e.g., is non-symmetric about the spindle axis). Such a lens may be described as having an independent elevation specific design in which the Z coordinate can be independently specified for each point on the lens surface. Such a design allows for the non-symmetric design of the elements of the lens including the landing zone and any bump zones or other features taken into consideration in the lens. In embodiments, the Z coordinate may vary along the entire perimeter of a lens.

The use of a non-symmetric lens design may allow the lens to rotate into alignment with the features of the eye. In general, various forces such as surface tension and interferences with the features of the eye can create a force that rotates the lens the proper alignment when placed on the eye. For example, the lens may rotate until the bump zones, if any, align with the bumps on the eye. As another example, a non-symmetric design of the landing zone may cause the lens to rotate on the eye until the landing zone profile matches the scleral profile of the user. The alignment may result in the lens rotating on the eye, which may cause some amount of blurred vision and disorientation. In order to limit or reduce the rotation of the lens, a marking or indicator can be included on the lens to indicate an approximate starting orientation. In an embodiment, a line or dot (e.g., a colored line or dot) can be placed on the lens to indicate the relative position of the lens when it is placed on the eye. For example, a dot may be placed in the landing zone to indicate the upwards position of the lens (e.g., the 6 o'clock position). By aligning this marking with the upwards position when donning the lens, the lens may be nearly aligned with the correct position and limit the amount of rotation needed to fully align the lens with the features of the eye. While described as being in the upwards position, the mark or line could be at any relative position on the lens. In an embodiment, the mark or line may be disposed on the landing zone or the edge lift zone in order to avoid interfering with the visual path through the lens.

When the lens has been created, it may be checked for the proper power, prescription, size, or the like. The lens can then be sent to the prescribing doctor. When the subject returns to the doctor, the lens can be dispensed and fitted on the subject. The doctor may perform their own check of the lens, and typically, another vision check is performed on the subject while the lens is being worn. If the lens is correct, the subject may retain the lens and use the lens to correct their vision problems. In some cases, the lens may need a minor variation in the design, fit, or prescription once it is dispensed by the doctor. If a minor change is needed, the doctor can send the request along with the corrections back to the application user. Since the scan of the impression can be maintained, a second impression is generally not needed. Rather, the second lens can be redesigned based on the doctor's input, and the second lens can then be manufactured and sent to the doctor. This process generally represents a significantly shortened fitting process relative to other scleral lenses. The impression process can be repeated over time (e.g., once a year) to track any changes in the surface of the eye, if needed.

In addition to designing the lens, the impressions can be used to build a database of information for various subjects. When the impression is received and scanned, various information about the subject can be recorded and stored in a data store along with the 3D points (e.g., X, Y, Z coordinates) file and the resulting lens design files. Information about the subject can include, but is not limited to, name, date of the impression, doctor's name, birthdate, identification of the eye belonging to the impression (e.g., OD, OS, etc.), the scanner identification, the scanner resolution, the pathology of the subject, any notes about the subject, a patent identifier (e.g., an ID number), prescription, and any combination thereof. The data store may allow for queries to be performed. This feature may allow a doctor to order new lenses without the need to perform an additional impression. In addition, the design application can begin with an existing lens design for an existing subject rather than beginning the design process from the beginning.

In addition to being used for individual patients, the data store may be queried and analyzed to determine various features of the subject population and the lens designs. Various features of the eye can be observed by a doctor. However, the features may not be quantifiable, and a statistical analysis of a patient population may not be generally known. It is expected that various averages may exist for a population of subjects needing scleral lenses. For example, the averages can include, but are not limited to, the average shape of the sclera, the average clearances needed for the lenses, the average diameters of the limbal perimeter, and the like. By analyzing the data and determining one or more averages, a standard set of lenses or lens designs could be generated. These designs may allow for storable quantities of the lenses to be created and maintained within a storage facility. This would allow for an off-the-shelf scleral lens to be sold to an average subject or used as a temporary lens, while allowing customized lenses to be created for those subjects in need of more specific modifications.

Figure 6:
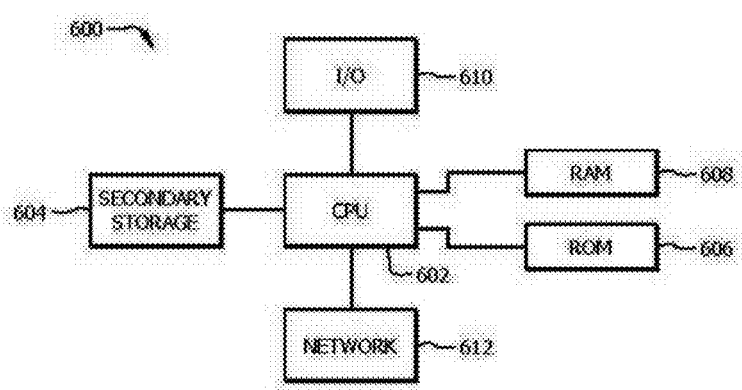
FIG. 6 illustrates an exemplary computer system suitable for implementing the several embodiments of the disclosure.

Various aspects of the systems described herein may be executed on a processor, for example, a processor in a computer system 600. For example, the design process including scanning the impression and designing the lens as well as various components of the lens manufacturing process may be implemented on a computer and/or the processor on a computer. FIG. 6 illustrates a computer system 600 suitable for implementing one or more of the embodiments of these processes as disclosed herein. The computer system 600 includes a processor 602 (which may be referred to as a central processor unit or CPU) that is in communication with memory devices including secondary storage 604, read only memory (ROM) 606, random access memory (RAM) 608, input/output (I/O) devices 610, and network connectivity devices 612. The processor 602 may be implemented as one or more CPU chips.

It is understood that by programming and/or loading executable instructions onto the computer system 600, at least one of the CPU 602, the RAM 608, and the ROM 606 are changed, transforming the computer system 600 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 604 is typically comprised of one or more disk drives or tape drives and is used for non-volatile storage of data and as an over-flow data storage device if RAM 608 is not large enough to hold all working data. Secondary storage 604 may be used to store programs, which are loaded into RAM 608 when such programs are selected for execution. The ROM 606 is used to store instructions and perhaps data, which are read during program execution. ROM 606 is a non-volatile memory device, which typically has a small memory capacity relative to the larger memory capacity of secondary storage 604. The RAM 608 is used to store volatile data and perhaps to store instructions. Access to both ROM 606 and RAM 608 is typically faster than to secondary storage 604. The secondary storage 604, the RAM 608, and/or the ROM 606 may be referred to in some contexts as computer readable storage media and/or non-transitory computer readable media.

I/O devices 610 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 612 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 612 may enable the processor 602 to communicate with an Internet or one or more intranets. With such a network connection, it is contemplated that the processor 602 might receive information from the network, or might output information to the network in the course of performing the above-described method steps. Such information, which is often represented as a sequence of instructions to be executed using processor 602, may be received from and outputted to the network, for example, in the form of a computer data signal embodied in a carrier wave.

Such information, which may include data or instructions to be executed using processor 602 for example, may be received from and outputted to the network, for example, in the form of a computer data baseband signal or signal embodied in a carrier wave. The baseband signal or signal embodied in the carrier wave generated by the network connectivity devices 612 may propagate in or on the surface of electrical conductors, in coaxial cables, in waveguides, in an optical conduit, for example an optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 602 executes instructions, codes, computer programs, scripts which it accesses from hard disk, floppy disk, optical disk (these various disk based systems may all be considered secondary storage 604), ROM 606, RAM 608, or the network connectivity devices 612. While only one processor 602 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 604, for example, hard drives, floppy disks, optical disks, and/or other device, the ROM 606, and/or the RAM 608 may be referred to in some contexts as non-transitory instructions and/or non-transitory information.

In an embodiment, the computer system 600 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 600 to provide the functionality of a number of servers that is not directly bound to the number of computers in the computer system 600. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 600, at least portions of the contents of the computer program product to the secondary storage 604, to the ROM 606, to the RAM 608, and/or to other non-volatile memory and volatile memory of the computer system 600. The processor 602 may process the executable instructions and/or data structures in part by directly accessing the computer program product, for example by reading from a CD-ROM disk inserted into a disk drive peripheral of the computer system 600. Alternatively, the processor 602 may process the executable instructions and/or data structures by remotely accessing the computer program product, for example by downloading the executable instructions and/or data structures from a remote server through the network connectivity devices 612. The computer program product may comprise instructions that promote the loading and/or copying of data, data structures, files, and/or executable instructions to the secondary storage 604, to the ROM 606, to the RAM 608, and/or to other non-volatile memory and volatile memory of the computer system 600.

In some contexts, a baseband signal and/or a signal embodied in a carrier wave may be referred to as a transitory signal. In some contexts, the secondary storage 604, the ROM 606, and the RAM 608 may be referred to as a non-transitory computer readable medium or a computer readable storage media. A dynamic RAM embodiment of the RAM 608, likewise, may be referred to as a non-transitory computer readable medium in that while the dynamic RAM receives electrical power and is operated in accordance with its design, for example during a period of time during which the computer 600 is turned on and operational, the dynamic RAM stores information that is written to it. Similarly, the processor 602 may comprise an internal RAM, an internal ROM, a cache memory, and/or other internal non-transitory storage blocks, sections, or components that may be referred to in some contexts as non-transitory computer readable media or computer readable storage media.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "about" means +10 percent of the subsequent number. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present invention.

What is claimed is:

1. An apparatus comprising:
 a lens configured to be disposed on an eye, wherein the lens comprises:
   a front lens surface;
   a back lens surface configured to engage a feature of a sclera of the eye to provide rotational stability of the lens on the eye; and
   an optical axis, and
 wherein the optical axis is not aligned with a corneal apical axis of the eye.

2. The apparatus of claim 1, wherein the lens comprises a scleral cover shell.

3. The apparatus of claim 1, wherein the lens comprises a decentered optical design.

4. The apparatus of claim 1, wherein the lens comprises an independent elevation specific design.

5. The apparatus of claim 1, wherein the back lens surface is determined according to an optic zone of the eye located within a limbal perimeter of the eye, a transition zone adjacent to the optic zone, a landing zone adjacent to the transition zone, and an edge lift zone adjacent to the landing zone.

6. The apparatus of claim 1, wherein the front lens surface is determined according to an optic zone of the eye located within a limbal perimeter of the eye, a transition zone adjacent to the optic zone, a landing zone adjacent to the transition zone, and an edge lift zone adjacent to the landing zone.

7. The apparatus of claim 1, wherein the front lens surface is determined according to the back lens surface.

8. A method of manufacturing a lens for disposition on an eye, comprising:
 identifying a corneal apical axis of the eye
 calculating characteristics of a back surface of the lens having an optical axis not aligned with the corneal apical axis of the eye and a portion configured to engage a feature of a sclera of the eye to provide rotational stability of the lens on the eye;
 calculating characteristics of a front surface of the lens having an optical axis not aligned with the corneal apical axis of the eye; and
 generating a lens design file for controlling a manufacturing device to manufacture the lens at least according to the calculated characteristics of the back surface of the lens.

9. The method of claim 8, further comprising generating the lens design file for controlling the manufacturing device to manufacture the lens at least according to the calculated characteristics of the front surface of the lens.

10. The method of claim 8, wherein the optical axis of the front surface of the lens is not aligned with the optical axis of the back surface of the lens.

11. The method of claim 8, wherein the optical axis of the front surface of the lens is aligned with the optical axis of the back surface of the lens.

12. The method of claim 8, wherein the lens comprises a scleral cover shell.

13. The method of claim 8, wherein the lens comprises a decentered optical design.

14. The method of claim 8, wherein the lens comprises an independent elevation specific design.

15. The method of claim 8, wherein the back lens surface is determined according to an optic zone of the eye located within a limbal perimeter of the eye, a transition zone adjacent to the optic zone, a landing zone adjacent to the transition zone, and an edge lift zone adjacent to the landing zone.

16. An apparatus comprising:
a front lens surface;
a back lens surface configured to engage a feature of a sclera of an eye to provide rotational stability of the lens on the eye;
a visual axis; and
an optical axis,
wherein the optical axis is not aligned with a corneal apical axis of the eye, and
wherein the visual axis is aligned with the optical axis.

17. The apparatus of claim 16, wherein the optical axis passes through a center of an optic zone of the front lens surface and the back lens surface.

18. The apparatus of claim 16, wherein a spindle axis of the apparatus is independent of the optical axis.

19. The apparatus of claim 18, wherein the device is non-symmetric about the spindle axis.

20. The apparatus of claim 16, wherein the back surface of the lens is determined according to an optic zone of the eye located within a limbal perimeter of the eye, a transition zone adjacent to the optic zone, a landing zone adjacent to the transition zone, and an edge lift zone adjacent to the landing zone.

* * * * *